United States Patent
Zimare et al.

(10) Patent No.: US 8,315,280 B2
(45) Date of Patent: Nov. 20, 2012

(54) MULTIWAVELENGTH LASER SYSTEM AND METHOD FOR OPHTALMOLOGICAL APPLICATIONS

(75) Inventors: Diego Zimare, Pausa (DE); Manfred Dick, Gefell (DE); Martin Wiechmann, Jena (DE); Alexander Kalies, Jena (DE); Regina Schuett, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 12/281,284

(22) PCT Filed: Apr. 20, 2007

(86) PCT No.: PCT/EP2007/003490
§ 371 (c)(1),
(2), (4) Date: Dec. 1, 2008

(87) PCT Pub. No.: WO2007/121943
PCT Pub. Date: Nov. 1, 2007

(65) Prior Publication Data
US 2009/0207874 A1  Aug. 20, 2009

(30) Foreign Application Priority Data
Apr. 25, 2006  (DE) .......................... 10 2006 019 127

(51) Int. Cl.
*H01S 3/30* (2006.01)
(52) U.S. Cl. ........... 372/6; 372/50.121; 372/108; 606/4; 606/11
(58) Field of Classification Search .................. 372/6
See application file for complete search history.

(56) References Cited

U.S. PATENT DOCUMENTS

| | | | |
|---|---|---|---|
| 4,759,360 A * | 7/1988 | Nakanishi et al. | 606/6 |
| 5,147,349 A * | 9/1992 | Johnson et al. | 606/4 |
| 5,243,983 A | 9/1993 | Tarr et al. | |
| 5,347,329 A | 9/1994 | Ota et al. | |
| 5,444,724 A * | 8/1995 | Goto | 372/20 |
| 5,669,934 A * | 9/1997 | Sawyer | 606/213 |
| 5,719,894 A | 2/1998 | Jewell et al. | |
| 5,817,088 A * | 10/1998 | Sterling | 606/4 |
| 5,867,305 A * | 2/1999 | Waarts et al. | 359/337.12 |
| 6,167,075 A * | 12/2000 | Craig et al. | 372/75 |

(Continued)

FOREIGN PATENT DOCUMENTS

DE  4225191  2/1993

(Continued)

OTHER PUBLICATIONS

F.G. Bachmann: "Chances and limitations of high power diode lasers", Proceedings of SPIE: High-power diode laser technology and applications II, SPIE, Bellingham, WA, USA, vol. 5336, pp. 95-105, 2004.

(Continued)

*Primary Examiner* — Patrick Stafford
*Assistant Examiner* — Xinning Niu
(74) *Attorney, Agent, or Firm* — Leydig, Voit & Mayer, Ltd.

(57) ABSTRACT

A multiwavelength laser system for opthalmological applications. The system including a first semiconductor diode laser including a first working beam of a first wavelength; and at least one second semiconductor diode laser having a second working beam of a second wavelength. The second wavelength being different from the first wavelength.

25 Claims, 4 Drawing Sheets

U.S. PATENT DOCUMENTS

| | | | |
|---|---|---|---|
| 6,258,082 B1 * | 7/2001 | Lin | 606/5 |
| 6,584,130 B2 * | 6/2003 | Hanke | 372/50.1 |
| 2004/0064022 A1 | 4/2004 | Korn | |
| 2004/0126272 A1 | 7/2004 | Bornstein | |
| 2005/0288565 A1 | 12/2005 | Kerr | |

FOREIGN PATENT DOCUMENTS

| | | |
|---|---|---|
| EP | 0980680 | 2/2000 |
| EP | 1184947 | 3/2002 |
| WO | WO-9112641 | 8/1991 |
| WO | WO-9514251 | 5/1995 |
| WO | WO-0221646 | 3/2002 |

OTHER PUBLICATIONS

Thorlabs Inc.:"Tools of the trade—catalogue", 2005, Thorlabs Inc., vol. 17, pp. 824-826, 854-857.

European Patent Office, International Search Report in International Patent Application No. PCT/EP2007/003490 (dated Oct. 8, 2007).

* cited by examiner

MULTIWAVELENGTH LASER SYSTEM AND METHOD FOR OPHTALMOLOGICAL APPLICATIONS

CROSS REFERENCE TO PRIOR APPLICATIONS

This application is a U.S. National Phase application under 35 U.S.C. §371 of International Application No. PCT/EP2007/003490, filed on Apr. 20, 2007 and claims benefit to German Patent Application No. DE 10 2006 019 127.7, filed on Apr. 26, 2006. The International Application was published in German on Nov. 1, 2007 as WO/2007/121943 under PCT Article 21 (2).

FIELD

The present invention relates to a multiwavelength laser system and to a method for ophthalmological applications. In particular, the present invention relates to a multiwavelength laser system which includes at least two semiconductor diode lasers and one light-guide system.

BACKGROUND

In medicine, in particular in ophthalmology, laser-based treatment systems are used to perform minimally invasive procedures on the human body. In this context, different laser wavelengths are used for different treatments on the eye. For example, when diode lasers are used, output powers in the range of approximately 400 mW in the long-wave spectral region of 690 nm are used for photodynamic treatments.

In ophthalmology, it is known to use high-power diode lasers, inter alia, for "transpupillary thermotherapy" (TTT), a wavelength of 810 nm being applied at an output power of approximately 650 mW.

Moreover, ophthalmological laser devices employ a diode laser that is operated in the red wavelength region at a non-damaging output power of less than 1 mW, as to produce what is commonly known as a pilot or alignment beam, in order to adjust the focus of the radiation to the specific application prior to applying the therapeutic useful radiation.

Various technical approaches from the non-ophthalmological sector are described in World Patent Applications WO 91/12641 and WO 95/14251, which provide for coupling two or more laser diodes into individual optical fibers.

One widely used ophthalmological laser therapy is what is commonly known as laser coagulation of the retina. It is used, for example, in the treatment of "diabetic retinopathy." Particularly of interest for modified therapies in this context are the green, yellow and red spectral regions which are covered by multiwavelength systems on the basis of gas lasers and purely diode-pumped and frequency-multiplied solid-state laser systems, as described in the World Patent Application WO 02/21646 A1 and the European Patent EP 1 184 947.

However, under the related art, multiwavelength systems disadvantageously necessitate a large volume, a large mass, a high complexity and a substantial energy demand and, at the same time, they give off considerable heat, resulting in increased costs for manufacturing, operating and maintaining such systems.

SUMMARY OF THE INVENTION

An aspect of the present invention is to provide a device and a method for use in ophthalmological applications, which will address the above mentioned disadvantages, be characterized by a broad wavelength spectrum and, respectively, be able to control a therapeutic application using various therapeutic approaches.

A multiwavelength laser system for ophthalmological applications is provided which has a first semiconductor diode laser having a first working beam of a first wavelength, and at least one second semiconductor diode laser having a second working beam of a second wavelength. The device according to the present invention allows for at least two wavelengths to be provided for ophthalmological applications and therapies, the multiwavelength laser system featuring a substantial compactness.

A multiwavelength laser system is a laser system which completely or partially emits a wavelength spectrum and which covers a range from the infrared to the UV region, for example. By employing at least two different wavelengths, it is possible to use the laser system for various therapy areas, such as photocoagulation, photodynamic therapy (PDT), transpupillary thermotherapy (TTT), photothermal tumor treatment, etc.

Ophthalmological applications are understood to include medical and cosmetic applications relating to ophthalmology, such as, for instance, the previously mentioned photocoagulation, photodynamic therapy (PDT), transpupillary thermotherapy (TTT), photothermal tumor treatment, etc.

A semiconductor diode laser is understood to be a diode laser or a diode laser in conjunction with additional, wavelength-influencing optical elements, whose active medium is made of a semiconductor material. In this context, as semiconductor materials, what are commonly known as compound semiconductors are mostly used, such as what are generally referred to as III-V semiconductors, such as gallium arsenide (GaAs) or indium antimonide (InSb), or semiconductors from the II. and VI. main group of the periodic system, i.e., what are generally referred to as II-VI semiconductors, such as zinc selenide (ZnSe) or cadmium sulfide (CdS). However, other combinations are also conceivable, such as GaInAsSb, AlGaAsSb, AlGaInP, AlAs, GaP, InAs, InP, doped garnets or doped vanadates.

The working beam is that beam which is emitted by the multiwavelength laser system and is needed for performing the ophthamological application, and which produces the desired effect in the eye. Thus, for example, in the case of trabeculotomy, a surgical method for removing glaucoma (green star), what is commonly referred to as a relieving incision is made on the eye by application of the working beam of the semiconductor diode laser or of a solid-state laser, in order to drain the intraocular fluid of the eye.

First and second wavelengths $\lambda_1$, $\lambda_2$ connote that the two wavelengths differ from one another, so that, depending on the particular application case, they may be used in a therapeutically targeted manner for different ophthalmological applications or various specific embodiments of an application. From the different wavelengths, the advantage is derived that one working beam of the first wavelength may be applied, for example, for the ophthalmological application under specific predefined boundary conditions, while the second working beam of a second wavelength may be used for the same ophthalmological application under different boundary conditions or at a different location in the eye.

First and at least second semiconductor diode lasers indicate that at least two semiconductor diode lasers are used with or without supplementary optical elements that are capable of controlling the wavelength, the wavelengths of the working beams of the semiconductor diode lasers differing from one another.

In another advantageous exemplary embodiment, it is preferred that the first working beam have a first pulse duration $t_1$, and the second working beam, a second pulse duration $t_2$. Here the advantage is derived that the working beams may be applied for different lengths of time to the object to be ophthalmologically treated.

Another advantageous exemplary embodiment of the present invention provides for the multiwavelength laser system to be operated in the CW mode (continuous wave mode). As a result, the benefit is derived that the working beam of the semiconductor diode laser is able to be uniformly ophthalmologically applied and for a longer period of time.

Another advantageous exemplary embodiment of the present invention provides for the multiwavelength laser system to be operated in the PW mode (pulsed-wave mode), i.e., the working beams are pulsed by the multiwavelength laser system. The PW mode is achieved, for example, through the use of suitable control systems which periodically interrupt the working beam over and over again, following certain time intervals. As a result, the benefit is derived that the working beam of the semiconductor diode laser is able to be uniformly ophthalmologically applied for brief time intervals.

Another advantageous exemplary embodiment of the present invention provides that the semiconductor diode laser include a crystal from the group: GaInAsSb, AlGaAsSb, AlAs, GaAs, GaP, InAs, AlGaInP, AlGaInP/GaAs InP, doped garnets or doped vanadates, or similar compounds for producing semiconductor structures or the just mentioned semiconductor structures in conjunction with supplementary, wavelength-influencing optical elements. In this case, the benefit is derived that the multiwavelength laser system makes it possible for different wavelength regions to be covered, which cannot be achieved by using conventional systems and which can be continuously tuned within certain limits by varying the operating parameters, thereby making it possible for the multiwavelength laser system to be used for different therapeutic sectors and the potentially different boundary conditions thereof. Moreover, the different semiconductor diode lasers preferably have different energy profiles and beam profiles.

Another advantageous exemplary embodiment of the present invention provides that at least one of the semiconductor lasers be replaceable by a laser system of active solid-state material and supplementary wavelength-influencing optical elements or by a doped wave-guiding optical material, for example an optical fiber, with or without supplementary wavelength-influencing elements.

Another advantageous exemplary embodiment of the present invention provides that wavelengths $\lambda_1$, $\lambda_2$ of the working beams reside within one of the following spectral regions: 480 nm to 520 nm, 530 nm to 550 nm, 560 nm to 580 nm, 585 nm to 615 nm, 620 nm to 670 nm, 685 nm to 695 nm, 800 nm to 820 nm, 1040 nm to 1070 nm. In this case, the benefit is derived that the multiwavelength laser system makes it possible for different wavelength regions to be covered, thereby making it possible for the multiwavelength laser system to be used for different therapeutic sectors. As a result, as already previously mentioned, the laser system may be selectively used for different therapy areas and for the various boundary conditions occurring in this context, such as photocoagulation, photodynamic therapy (PDT), transpupillary thermotherapy (TTT), photothermal tumor treatment, etc.

Another advantageous exemplary embodiment of the present invention provides that the energies of the working beams be distinct from one another. In this case, the advantage is derived that the multiwavelength laser system may be used for different therapeutic sectors where different energies are required. It is thus conceivable, for example, for there to be one higher-energy working beam for the laser trabeculotomy (ALT, DLT, LT) and one working beam having mostly low energy deviating therefrom for the selective laser trabeculotomy (SLT).

Another advantageous exemplary embodiment of the present invention provides that the working beams have energies of between 10 µJ and 50 J, preferably between 0.5 mJ and 25 J, and most preferably of between 0.5 mJ and 20 J. Here, the advantage is derived that the working beams may be used for different ophthalmological applications and therapies as a function of the specific application and selectively in terms of different boundary conditions.

Another advantageous exemplary embodiment of the present invention provides that the energies of the working beams be between 10 µJ and 50 J, preferably between 0.5 mJ and 25 J, and most preferably between 0.5 mJ and 20 J, and that the wavelengths originate from a region that includes the previously mentioned wavelength intervals. Here, the advantage is derived that the working beams may be used for different implementations of the same ophthalmological applications and therapies, since working beams of a different pulse duration and same wavelength are used.

Another advantageous application example of the present invention provides that the energies of the working beams be between 10 µJ and 50 J, preferably between 0.5 mJ and 25 J, and most preferably between 0.5 mJ and 20 J, that the wavelengths originate from a region that includes the previously mentioned wavelength intervals, and that the laser sources be composed of combinations of active solid-state media having wavelength-influencing optical elements. Here, the advantage is derived that the working beams may be used for different implementations of the same ophthalmological applications, but for different therapeutic approaches, since working beams of various pulse duration regimes (ms-, µs- or ns regimes) may be used.

Another advantageous exemplary embodiment of the present invention provides that a beam parameter product of the semiconductor diode laser be within a range of order of magnitude of between 0.1 and 125 mm*mrad, preferably between 1 and 100 mm*mrad, and most preferably of between 2 and 80 mm*mrad. Here, the advantage is derived that the working beams may be coupled into one or a plurality of optical fibers and be used for different ophthalmological applications and therapies as a function of the specific application, since the beam parameter product defines the quality of the laser beam on the basis of the focusability thereof.

Another advantageous exemplary embodiment of the present invention provides that at least one of the working beams have a pulse duration of between 1 femtosecond (1 fs) to 600 seconds, preferably between 1 picosecond (1 ps) and 500 seconds, and most preferably of between 1 nanosecond (1 ns) and 300 seconds. In this case, the advantage is derived that the multiwavelength laser system may be used for user-specific therapeutic applications.

Another advantageous exemplary embodiment of the present invention provides that the working beams of the semiconductor diode lasers or of the semiconductor diode lasers in conjunction with supplementary, wavelength-influencing optical elements, or the laser sources composed of combinations of active solid-state media having wavelength-influencing optical elements be controllable separately from one another. Separately controllable connotes that the semiconductor diode lasers are driven by a user interface, as well as by a corresponding external control in such a way that only the one semiconductor diode laser or the other semiconductor diode laser may be alternately driven, a working beam then being emitted by the corresponding semiconductor diode laser. Of course, it is also possible that both semiconductor diode lasers be driven simultaneously and that corresponding working beams of different wavelengths be emitted simultaneously. Moreover, the working beams of the semiconductor diode lasers may also be controlled in such a way that the working beams thereof are able to be spatially offset in one plane, for example through the use of a scanner. From the separate control, the advantage is derived that the working beams may be used for different ophthalmological applications as a function of the specific application. For example, the working beams may be applied in a temporally offset manner or simultaneously. It is likewise conceivable that the working beams be used in a spatially offset manner in the ophthalmological application, the first working beam being used for the ophthalmological application, the spatially shifted or temporally offset second working beam for the pretreatment and/or posttreatment of the ophthalmologically treated tissue. It is likewise conceivable for the working beams for the ophthalmological application to be radiated in a preprogrammed process, the treatment sequences taking place simultaneously or separately in time.

Another advantageous exemplary embodiment of the present invention provides that the working beams emitted by the semiconductor diode lasers be linearly polarized. Here, the advantage is derived that at least two of the working beams or at least one working beam of at least two available working beams and at least one working beam are mechano-optically superposed and may be coupled into an additionally connected light-guide system. In particular, the component beams may be superposed in such a way that their beam parameter products are not degraded in the process.

In accordance with another aspect of the present invention, a light-guide system is provided which includes at least one fiber-optic system, the working beams of a multiwavelength laser system being couplable into the light-guide system via the fiber-optic system. Here the advantage is derived that the ray path of the working beams is not exposed, as in the case of a mechanico-optical system, and the entire optical system is, therefore, less susceptible to faults. For example, environmental influences, such as dust or moisture, can interact with the optical components, thereby affecting the overall performance of the system and entailing a substantial outlay for inspections, recalibrations, etc. on a regular basis.

In this context, a light-guide system is understood to be a device, for example an optical fiber, a fiber-optic system or an array of optical elements, which allows electromagnetic waves, in particular light from the IR region to the UV region, to propagate from one end of the device to the other.

A fiber-optic system is an optical system which includes at least one optical fiber, as a result, the light ray path no longer being exposed, as in the example of mechanico-optical systems. In this context, a mechanico-optical system is understood to be an optical system in which the ray paths are exposed and are not received in an optical fiber, for example, thereby resulting in numerous disadvantages due to the environmental influences acting on the optical system. These disadvantages are overcome by the fiber-optic system provided by the present invention.

The designation "couplable" is understood to mean that the working beams of the semiconductor diode laser are focused into the optical fiber of the light-guide system in a way that allows them to propagate within the optical fiber without any substantial loss of intensity. The aim in this context is for the working beams to be coupled into the light-guide system in a way that does not permit any appreciable loss of energy of the working beams.

Another advantageous exemplary embodiment of the present invention provides that the fiber-optic system include at least one optical fiber. Here, the advantage is derived that the working beams are able to be transmitted via the fiber-optic system in an optimized and cost-effective process.

In accordance with another advantageous exemplary embodiment of the present invention, the fiber-optic system may include at least two optical fibers which are coupled to form one optical fiber. Here, the advantage is derived that the working beams from different radiation sources, for example semiconductor diode lasers, may be superposed or merged at one fiber outlet.

Another advantageous exemplary embodiment of the present invention provides that a beam parameter product of at least one fiber of the fiber-optic system be within a range of order of magnitude of between 0.1 and 125 mm*mrad, preferably between 1 and 100 mm*mrad, and most preferably of between 2 and 80 mm*mrad. Here, the advantage is derived that the working beams from a plurality of beam radiation sources, for example semiconductor diode lasers, may be coupled into one or a plurality of optical fibers and be used for different ophthalmological applications and therapies as a function of the specific application, since the beam parameter product defines the quality of the laser beam on the basis of the focusability thereof.

Another advantageous exemplary embodiment of the present invention provides that the working beams be couplable into the fiber-optic system at any given locations on the same. Here the advantage is derived that the light-guide system is adaptable to the particular ophthalmological laser therapy as a function of the specific application. Thus, for example, a supplementary pilot beam may also be coupled into the optical fiber at any given location on the same to aid the ophthalmological application. Conversely, one or more working beams are couplable out of the light-guide system, for example, in order to measure the power thereof using a power detector.

Another advantageous exemplary embodiment of the present invention provides that the working beams be partially couplable out of the fiber-optic system at at least one given location on the same. This allows one or a plurality of working beams to be coupled out of the light-guide system in order to detect or monitor the power thereof using a power detector or control the same via a closed-loop control circuit, for example.

Another advantageous exemplary embodiment of the present invention provides that at least one fiber of the fiber-optic system have a diameter of between 5 μm and 500 μm, preferably of between 20 μm and 250 μm, and most preferably of between 50 μm and 100 μm. The ability to transmit working beams having the appropriate energy levels and requisite beam parameter product is advantageously derived in this case.

Another advantageous exemplary embodiment of the present invention provides that, at its distal end, the optical fiber system be at least a single-core fiber, which has at least one fiber core having a core diameter of between 10 μm and 600 μm, preferably of between 30 μm and 400 μm, and most preferably of between 40 μm and 160 μm. The ability to transmit working beams having the appropriate energy levels and requisite beam parameter product to the application site is advantageously derived in this case.

In accordance with another advantageous exemplary embodiment of the present invention, the numerical aperture (N.A.) of the fiber core of at least one fiber of the fiber-optic system at the proximal ends and at the distal end thereof is between 0.01 and 0.4, preferably between 0.05 and 0.22, and most preferably between 0.07 and 0.15. Here, the advantage is derived that the light-guide system is able to efficiently transmit radiation for ophthalmological applications and for the optical requirements thereof.

In accordance with another advantageous exemplary embodiment of the present invention, the fiber-optic system is coupled to a mechanico-optical system to enable the beam parameters of the laser source, for example of the semiconductor laser and the fiber-optic system, to be adapted. In this way, the energy is able to be transferred from the laser source to the application site at a minimal loss.

Another advantageous exemplary embodiment of the present invention provides that at least one fiber of the fiber-optic system have a doping. Here, the advantage is derived that at least one of the working beams from the already mentioned wavelength regions is generated, wavelength-converted, or amplified directly in the fiber-optic system. As a result, the complexity of the entire system may be advantageously reduced.

Another advantageous exemplary embodiment of the present invention provides that at least one fiber of the fiber-optic system be doped and be configured as a double-core fiber. This advantageously makes it possible for losses to be minimized when the laser sources are coupled into the fiber-optic system.

In accordance with another advantageous exemplary embodiment of the present invention, a pilot beam, which is emitted from a semiconductor laser diode or from a semiconductor light-emitting diode, is couplable into the light-guide system. Here the advantage is derived that the working beams of the multiwavelength laser system may be selectively ophthalmologically applied in combination with the light-guide system, since the working beams are not visible to the user before or during the application, and thus the exact position of the working beams is made visible before and during the application, thereby ensuring the safety of the system.

Another advantageous exemplary embodiment of the present invention provides that the pilot beam have a power of less than 1 mW, preferably of less than 0.1 mW. Here, the benefit is derived that the pilot beam does not damage the ophthalmologically treated tissue since it merely has a supporting function in the ophthalmological laser therapy and serves the purpose of precisely visually aligning the area to be ophthalmologically treated later by the working beams.

Another advantageous exemplary embodiment of the present invention provides that an application fiber be connectable to one or a plurality of fibers of the fiber-optic system. Depending on the ophthalmological application, the application fiber may be introduced directly into the eye, for example, or constitute a part of the light-guide system. The therapeutic process supported by the multiwavelength laser system may be subsequently begun. Through the use of an application fiber, the advantage is derived that the light-guide system may be optimized for ophthalmological applications as a function of the specific application, and the working beams of the multiwavelength laser system may be used more precisely for the object to be ophthalmologically treated.

In accordance with another advantageous exemplary embodiment of the present invention, the beam parameter product of the fiber-optic system is smaller than or equal to that of the application fiber. Here, the advantage is derived that the working beams penetrating the fiber-optic system are able to be optimally coupled into the application fiber.

Another advantageous exemplary embodiment of the present invention provides that the fiber-optic system be composed at its distal end of more than one fiber and that it include a fiber-optic or mechanico-optical component which may be used for switching, respectively distributing the incoupled working beams between outlets of the fiber-optic system.

Another advantageous exemplary embodiment of the present invention provides that the fiber-optic system and the light-guide system include at least one polarization-maintaining optical fiber. Here the advantage is derived that the working beams intended for use in various therapeutic applications are coupled into the light-guide system and may be superposed therein as a function of polarization without any significant loss of energy or power of the working beams.

Another advantageous exemplary embodiment of the present invention provides that the fiber-optic system include at least one mechanico-optical system. A mechanico-optical system is understood to be an optical system in which the ray paths are exposed and are not received in an optical fiber, for example, thereby entailing numerous disadvantages due to environmental influences acting on the optical system. However, the mechanico-optical system also provides the advantage that the light-guide system is individually adaptable to specific ophthalmological applications, thereby enhancing the flexibility of the light-guide system.

Another advantageous exemplary embodiment of the present invention provides that the light-guide system include at least one dichroic coupler. A dichroic coupler is understood to be a device whose optical system transmits light of one precisely defined wavelength region and reflects light of another precisely defined wavelength region. Here the advantage is derived that the working beams are able to be superposed within the light-guide system.

Another advantageous exemplary embodiment of the present invention provides that the laser system include at least one power control and power monitoring. In the following, laser system connotes the totality of all components of the multiwavelength laser system and of the light-guide system. The purpose of the power monitoring is to monitor the power of the working beams coupled by the multiwavelength laser system into the light guide system at a specific location on the optical fiber to ensure that the working beams at the end of the optical fiber exhibit an appropriate energy and power which is later applied via the application fiber during the ophthalmological application. If the actual energy and power deviate from that which is desired and required for the treatment, the power control causes the semiconductor diode laser to be driven in a feedback loop in such a way that the energy and power necessary for the ophthalmological application are produced in the optical fiber and at the fiber end. Here the advantage is derived that the light-guide system, together with the multiwavelength laser system, may be adjusted for ophthalmological applications as a function of the specific application, that the light-guide system and the working beams coupled by the multiwavelength laser system into the light-guide system may be continually monitored, and that any parameter modifications to the system that become necessary may be undertaken.

Another advantageous exemplary embodiment of the present invention provides that the laser system include at least one system control. The system control is required for the previously mentioned power monitoring and power control to enable the semiconductor diode laser to be properly driven, in order that the working beam energies required for the laser therapy application may be achieved. In this context, the system control includes drivers, sensors, monitoring and control electronics, an electronic computer and corresponding control software. Here the advantage is derived that the light-guide system, together with the multiwavelength laser system, may be adjusted in a feedback loop as a function of the specific ophthalmological application.

Another advantageous exemplary embodiment of the present invention provides that the light-guide system include at least one optical mirror. In this context, optical mirrors are designed to completely reflect the laser light of the working beams or only a portion of the incident light. As preferred optical mirrors, mirrors that are customarily used for ray paths produced by semiconductor diode lasers are used. The optical mirrors are also used for coupling the working beams into the fiber-optic system in a first step using a mechanico-optical system should this be necessitated by the relevant local conditions. The use of optical mirrors advantageously allows the light-guide system and/or the laser system to be set up for ophthalmological applications as a function of the specific application.

Another advantageous exemplary embodiment of the present invention provides that the laser system include a system for evaluating backscattered and/or partially reflected working beams. The system for evaluating such backscattered and/or partially reflected beams may be set up to allow the incoupled energy and power in the case of the optical fiber and/or the light-guide system to be compared to the outcoupled energy and power at the end of the optical fiber. If the ratio between the incoupled and outcoupled energy and power is within a certain empirically ascertained interval, then no correction to this effect is applied by the system via the previously mentioned system control. However, if the ratio deviates too greatly from the relevant values, the light-guide system is corrected by the system for evaluating the backscattered and/or partially reflected working beams until the desired ratio is reached. When a system for evaluating backscattered and/or partially reflected working beams is used, the advantage is derived that the working beams from the multiwavelength laser system coupled into the light-guide system may be continually monitored and any parameter modifications to the system that become necessary may be undertaken to ensure that working beam states that are dangerous to the user of the light-guide system do not occur and that the ophthalmological application of the system is optimized.

Another advantageous exemplary embodiment of the present invention provides that the laser system include a remote control. A remote control is understood to mean, for example, that the multiwavelength laser system, in conjunction with the light-guide system, is also monitored and controlled from a location that is remote from the application site, by an appropriate terminal (computer, touch pad, Bluetooth device, etc.). Here the advantage is derived that the multiwavelength laser system may also be operated and controlled in the case of an application that is set up at a more remote location.

Another advantageous exemplary embodiment of the present invention provides that the beam parameter product of the working beams of the semiconductor diode lasers be smaller than or equal to the beam parameter product of the light-guide system and smaller than 125 mm*mrad. Here the advantage is derived that the working beams are optimally couplable into the light-guide system, thereby permitting an adaptive utilization of the light-guide system. In accordance with another advantageous exemplary embodiment of the present invention, the beam parameter product at the fiber coupling sites of the light-guide system is comparable to the beam parameter product of the semiconductor diode laser. Here the advantage is derived that the working beams are optimally couplable into the light-guide system.

Another advantageous exemplary embodiment of the present invention provides that the laser system include a control of the semiconductor diode laser, a user interface and an application system. The control presented in this context corresponds to the previously described system control; the user interface is the interface between the user of the system and the system control; and the application system is the interface between the semiconductor diode system and the patient. The light-guide system including the optical fiber, a slit lamp, an application fiber, etc., for example, may be disposed within the application system. In addition, the working beams may be coupled into the application system via two optical fibers. Here the advantage is derived that the light-guide system, together with the multiwavelength laser system, is able to be operated simply and cost-effectively.

Another advantageous exemplary embodiment of the present invention provides that the light-guide system have a slit lamp that is capable of projecting the laser light of the plurality of wavelengths of the working beams in an identical manner into the eye, given the same required treatment parameters. The slit lamp is an important tool in ophthalmology. With the assistance thereof, precise details may be seen in the front region of the eye. Numerous diseases of the eye, such as inflammation, cataracts, etc., may be identified by employing an adjustable magnification and special lateral illumination, what is generally known as the light slit. The slit lamp is used during the ophthalmological application to control the treatment and to apply the laser energy of the various working beams into the eye. Here the advantage is derived that the light-guide system is optimized by the slit lamp for ophthalmological applications which require different wavelengths, so that the therapeutic process is improved.

Another advantageous exemplary embodiment of the present invention provides that the working beams that are couplable into the light-guide system be able to be at least partially outcoupled, in particular couplable into a power monitoring. In this context, it is preferred that the working beams be able to be outcoupled from the light-guide system at a certain percentage of their intensity, for example 1%, and preferably be couplable into a power monitoring. From the partial outcoupling, the advantage is derived that there is no need to interrupt the application of the working beams to an area to be ophthalmologically treated. A power monitoring is preferably a mechanical or electronic device for determining the energy and/or the power of the working beams emitted by the multiwavelength laser system.

Another advantageous exemplary embodiment of the present invention provides that the power and/or energy of the first semiconductor diode laser and/or of the second semiconductor diode laser be adjustable by a power control via a control. Once the energy and/or the power of the working beams is ascertained by the power monitoring, the energy and/or the power are/is automatically or manually adjusted by a power control, which is preferably linked to the power monitoring, in that the actual value of the working beams to be applied is compared to the setpoint value of the energy and/or power required for the ophthalmological treatment.

If the actual value and setpoint value do not correspond, the power control transmits a signal to the control of the multiwavelength laser system, the energy and/or power being modified by a certain value as a function of the difference between the actual and the setpoint value. This modification is subsequently registered by the power monitoring and transmitted to the power control.

If the actual and setpoint values continue to deviate from one another, then the power control once again modifies the energy and/or the power of the multiwavelength laser system by transmitting a signal to the control of the multiwavelength laser system to effect a specific modification to the power and/or energy of the multiwavelength laser system. Due to the continuous comparison between the actual and setpoint values carried out by the power monitoring and the continuous signal transmission of the power control to the control of the multiwavelength laser system, a type of feedback results until the requisite setpoint value conforms with the instantaneous actual value of the multiwavelength laser system, up to a certain mutual percentage deviation.

Another advantageous exemplary embodiment of the present invention provides that the semiconductor diode laser be couplable by two separately adapted laser oscillators into the light-guide system. In this context, a laser oscillator is used for applying the working beams in the case of photocoagulation/ALT in the CW mode (continuous wave mode) and the second laser oscillator for applying the working beams in the PW mode (pulsed wave mode) in the case of selective trabeculotomy (SLT). The laser oscillators may have a common control, a common user interface, and a common application system (for example a slit lamp), for example. In the same way, a two-part shared application system composed of a slit lamp and a link system for the SLT may be used. The working beams may be fed to the application system via one, respectively two light-guide fibers, for example. In the same way, in the case of the application for the SLT, the multiwavelength laser system may be directly coupled to the application system. The optional configurations mentioned in the context of this exemplary embodiment advantageously make it possible for the working beams to be coupled in, in the CW mode or in the PW mode, at the appropriate pulse rate.

Another advantageous exemplary embodiment of the present invention provides that the light-guide system include a two-part application system that includes a slit lamp and a link system for selective laser trabeculotomy (SLT) that are mechanically coupled to one another. The slit lamp is used on the basis of the preceding explanations. The link system for laser trabeculotomy (SLT) permits the additional use of the multiwavelength laser system in the PW mode and in the case of another required beam parameter product of the application. Here the advantage is derived that the light-guide system may be used in a simple manner for different ophthalmological applications.

The objective is also achieved by a method for ophthalmological applications, in particular selective laser trabeculotomy (SLT) and/or laser trabeculotomy (ALT, DLT, LT), a multiwavelength laser system and/or a light-guide system in accordance with the preceding explanations being used. This advantageously improves the selective laser trabeculotomy (SLT) and/or laser trabeculotomy (ALT, DLT, LT) for relevant ophthalmological laser therapies and renders them more cost-effective.

In this context, the multiwavelength laser system preferably includes semiconductor diode lasers which contain a semiconductor crystal that originates from the group that includes: GaInAsSb, AlGaAsSb, AlAs, GaAs, GaP, InAs, AlGaInP, AlGaInP/GaAs, InP, doped garnets or doped vanadates, YAG, Nd:YAG.

The working beams of the semiconductor diode lasers are preferably couplable by two separately adapted laser oscillators into the light-guide system. In this context, a laser oscillator is used for applying the working beams in the case of photocoagulation/ALT in the CW mode (continuous wave mode) and the second laser oscillator for applying the working beams in the PW mode (pulsed wave mode) in the case of selective trabeculotomy (SLT).

The laser oscillators may preferably have a common control, a common user interface, and a common application system (for example a slit lamp). The laser oscillators, the multiwavelength laser, the common control, the common user interface and the common application devices may preferably be composed of one device unit, i.e., of one device.

In the same way, a two-part shared application system composed of a slit lamp and a link system for the SLT, for example, may preferably be used.

The working beams may be fed to the application system via one, respectively two light-guide fibers, for example. In the same way, in the case of the application for the SLT, the multiwavelength laser system may be directly coupled to the application system.

The optional configurations mentioned in the context of this exemplary embodiment advantageously make it possible for the working beams to be coupled in, in the CW mode or in the PW mode, at the appropriate pulse rate.

BRIEF DESCRIPTION OF THE DRAWINGS

Other advantageous embodiments of the present invention are clarified in the following with reference to the drawing, whose figures show:

FIG. 1 shows a schematic view of multiwavelength laser system 1 and of light-guide system 2 of the present invention.

DETAILED DESCRIPTION

In this context, multiwavelength laser system 1 is composed of the two semiconductor diode lasers 10.1 and 10.2 which emit working beams 20.1 and 20.2 having wavelengths $\lambda_1$ and $\lambda_2$.

Figure 1:
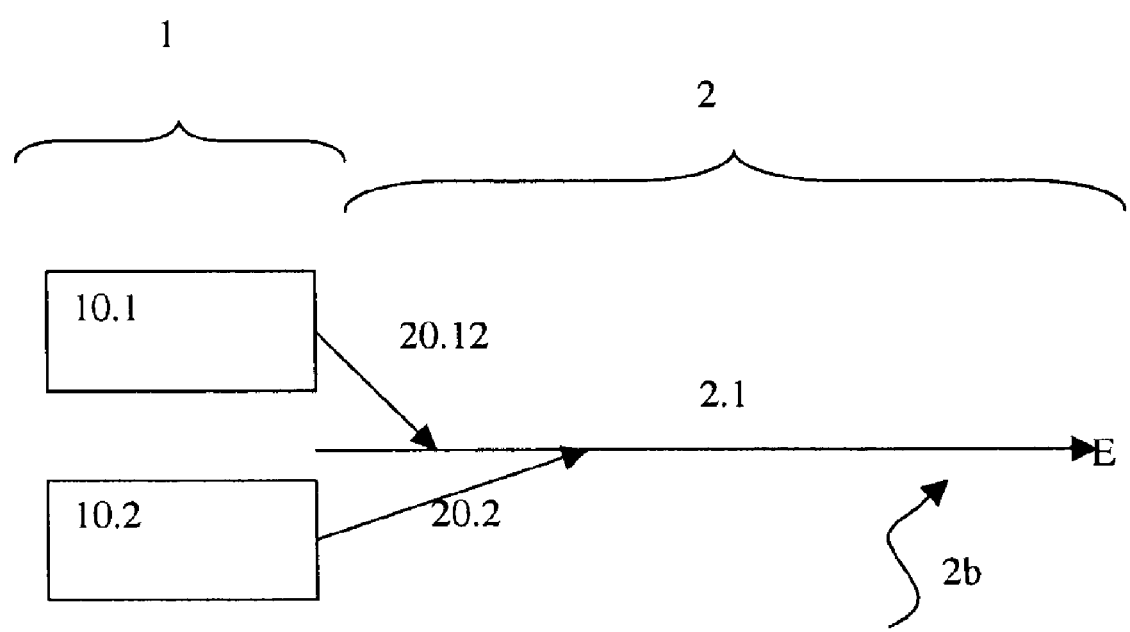
FIG. 1: a schematic representation of the multiwavelength laser system and of the light-guide system of the present invention.

Also illustrated in FIG. 1 is light-guide system 2 which includes an optical fiber 2.1; due to the use of an optical fiber 2.1 in the example illustrated here, light-guide system 2 being what is commonly known as a fiber-optic system.

Working beams 20.1 and 20.2 emitted by semiconductor diode lasers 10.1 und 10.2 are coupled at the same or different locations on optical fiber 2.1 into light-guide system 2 and subsequently propagate through optical fiber 2.1 until being coupled out at end E of optical fiber 2.1, which is composed of at least one fiber core, thereby making them available for ophthalmological applications.

Wavelength $\lambda_1$ of working beam 20.1 of the first semiconductor diode laser, which in this exemplary embodiment is an InGaAlP laser, is 635 nm; wavelength $\lambda_2$ of working beam 20.2 of the second semiconductor diode laser, which, in this exemplary embodiment, is a GaAlAs laser, is 820 nm.

The energy of first working beam 20.1 is 0.5 mJ; the energy of second working beam 20.2 is 4 J.

Moreover, first working beam 20.1 is operated in the CW mode; second working beam 20.2 in the PW mode, it being interrupted at regular intervals by a beam interrupter (laser shutter).

Given the preceding parameters, working beams 20.1 and 20.2 are suited for different ophthalmological applications, such as photocoagulation, photodynamic therapy (PDT), transpupillary thermotherapy (TTT), photothermal tumor treatment, etc.

In addition, the beam parameter product of working beams 20.1 and 20.2 of semiconductor diode lasers 10.1, 10.2 is 11 mm*mrad.

In addition, working beams 20.1, 20.2 of semiconductor diode lasers 10.1, 10.2 of the multiwavelength laser system are controllable separately from one another; this means that the emission thereof takes place in a temporally offset manner, first working beam 20.1 impinging on the object to be ophthalmologically treated carrying out a first ophthalmological treatment, and second temporally offset working beam 20.2 carrying out a corresponding ophthalmological posttreatment.

Moreover, working beams 20.1, 20.2 emitted by semiconductor diode lasers 10.1, 10.2 are linearly polarized to be more readily couplable into light-guide system 2.

Optical fiber 2.1 preferably has a diameter of 100 µm.

Figure 2:
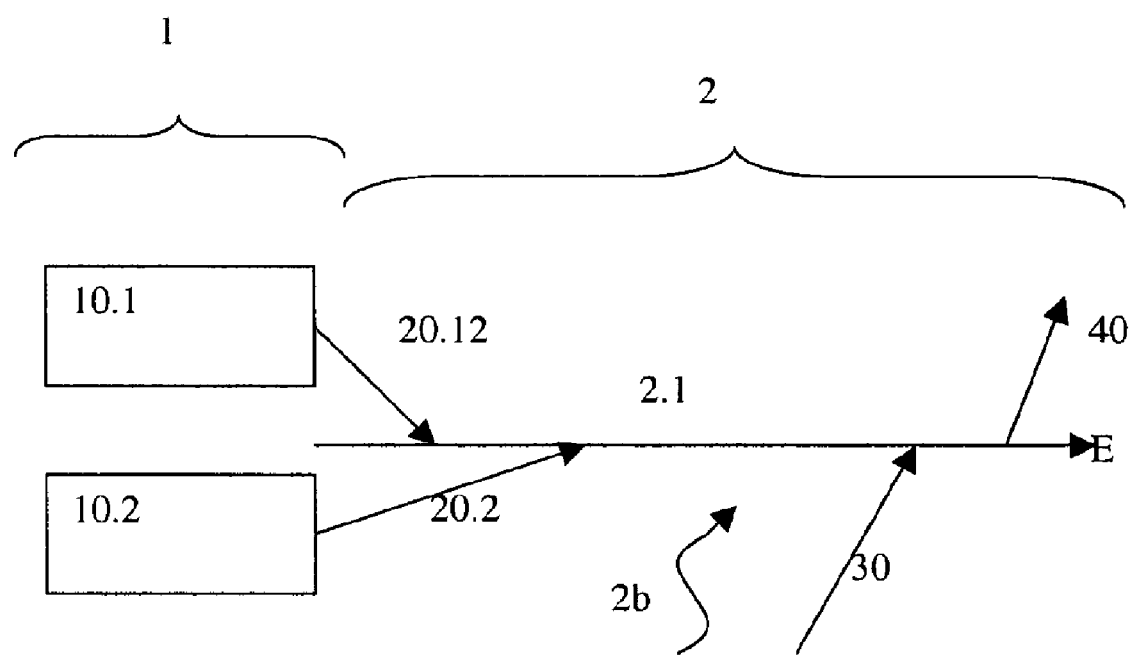
FIG. 2: the schematic view of the present invention illustrated in FIG. 1 including a supplementary pilot beam and power monitoring.

FIG. 2 shows another preferred specific embodiment of multiwavelength laser system 1 and of light-guide system 2.

In addition to multiwavelength laser system 1 and light-guide system 2 illustrated in FIG. 1, the device according to the present invention has at least one additional input on the fiber-optic system, for example for a pilot beam 30 or an additional working beam, and at least one additional output exhibiting partial outcoupling of 0-100 percent for a power monitoring 40, for example.

In the case of the device illustrated in FIG. 2, working beams 20.1 and 20.2 are likewise coupled into optical fiber 2.1 of light-guide system 2 and propagate through optical fiber 2.1 until being coupled out again from light-guide system 2 at end E of this optical fiber 2.1, thereby making them available for ophthalmological applications.

To provide operative assistance in ophthalmological applications, a pilot beam 30, which has a wavelength of 600 nm to 670 nm and a power of less than 0.5 mW, is coupled in. In this context, the pilot beam is preferably a light source based on semiconductor technology, for example a semiconductor diode laser.

Pilot beam 30 makes it possible for a user of the multiwavelength laser system and of the light-guide system to aim in advance at the later position of working beams 20.1 and 20.2 on the region of the eye to be ophthalomologically treated and to thereby make the laser system even safer for ophthalmological applications.

A power monitoring 40 is also provided, in this case, the working beams being able to be completely or partially coupled out, so that, prior to and during an ophthalmological application, it is possible to determine and control the power with which working beams 20.1 or 20.2 propagate through optical fiber 2.1. In this context, it is possible for the power of the working beams 20.1 and 20.2 to be improved by optimizing the beam path or for the power of working beams 20.1 and 20.2 to be reduced by controlling lasers 10.1 and 10.2. A control of this kind is described further below with reference to FIG. 4. The working beams are preferably also able to be coupled in separately.

Figure 3:
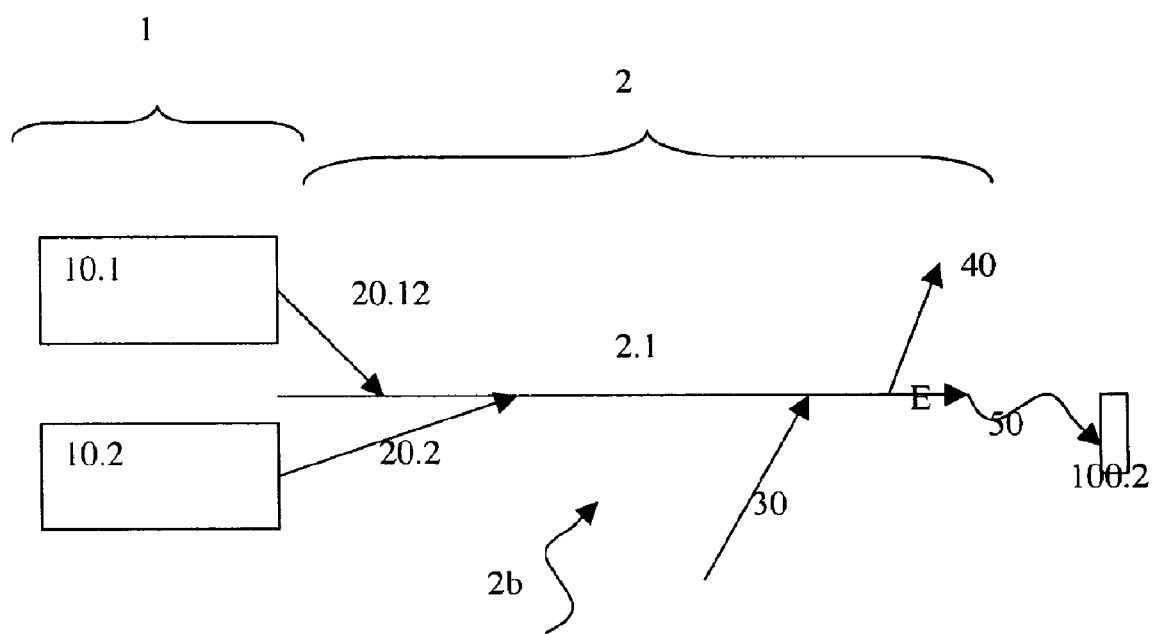
FIG. 3: the schematic view of the present invention illustrated in FIG. 2 including a supplementary light-guide system, along with an application fiber.

FIG. 3 represents another preferred specific embodiment of the multiwavelength laser system of the present invention.

In this context, in addition to the configuration of the multiwavelength laser system including the light-guide system at end E of optical fiber 2.1 illustrated in FIG. 2, a light-guide system having an application fiber 50 and an application system 100.2 are connected. This constitutes an interface between optical fiber 2.1 and the eye to be ophthalmologically treated. In this exemplary embodiment, application system 100.2 includes a slit lamp which enables more precise details of the front part of the eye to be seen.

In the configuration of multiwavelength laser system 1 and light-guide system 2 illustrated in FIG. 3, working beams 20.1 and 20.2 emitted by semiconductor diode lasers 10.1 and 10.2 are first coupled into optical fiber 2.1 of light-guide system 2, light-guide system 2 being a fiber-optic system 2b, and working beams 20.1 and 20.2 being couplable into optical fiber 2.1 at the same or different locations on the same.

Incoupled working beams 20.1 and 20.2 continue past the location in optical fiber 2.1 where a pilot beam 30 may be coupled in to aid the ophthalmological application, then pass by the location in optical fiber 2.1 where a power monitoring 40 is connected and where the energy and the power of the working beams may be monitored.

Once working beams 20.1 and 20.2 have reached end E of optical fiber 2.1, they pass directly into application fiber 50. In this context, application fiber 50 is connected in such a way that no appreciable loss in the energy or power of working beams 20.1 and 20.2 occurs.

With respect to its dimensioning and material properties, application fiber 50 is designed for ophthalmological applications in such a way that the previously described ophthalmological applications may be optimized at the eye and implemented as a function of the specific application. Application fiber 50 may preferably be introduced into the eye of a patient; thus a suitable ophthalmological application inside of the eye is possible.

Figure 4:
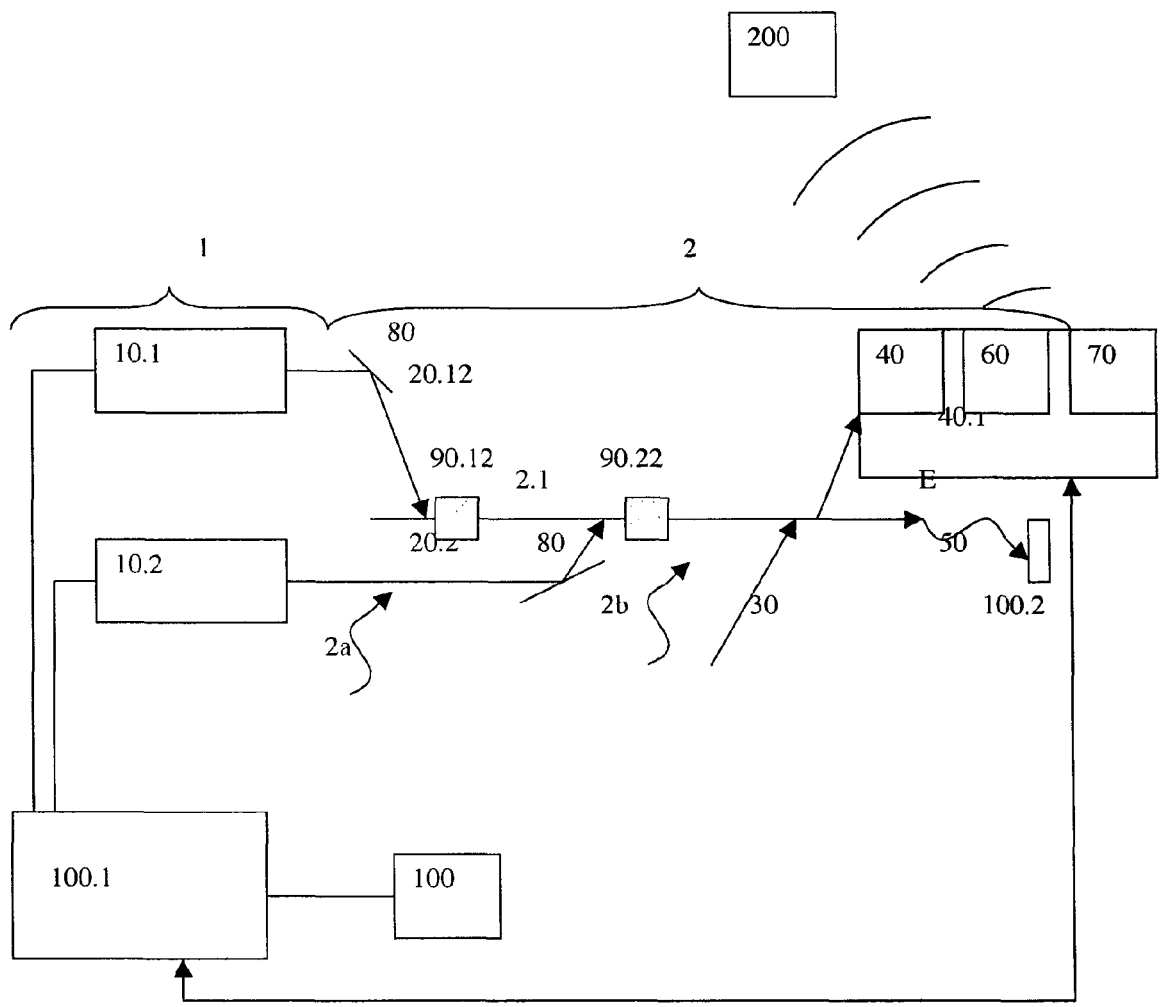
FIG. 4: the schematic view of the present invention illustrated in FIG. 3, including a supplementary mechanico-optical system, doping, control and user interface.

FIG. 4 illustrates an especially preferred specific embodiment of multiwavelength laser system 1 and of light-guide system 2 of the present invention.

In this context, multiwavelength laser system 1 is composed of the two semiconductor diode lasers 10.1 and 10.2, a user interface 100 and a control 100.1. As already described in FIG. 1, semiconductor diode lasers 10.1 and 10.2 are constituted of an InGaAlP laser and a GaAlAs laser having the specified parameters.

In this specific embodiment, in addition to optical fiber 2.1, light-guide system 2 includes a mechanico-optical system 2a, which is composed of optical mirrors 80, but also of refractive optical systems.

In addition, light-guide system 2 includes a fiber-optic system 2b, which is composed of optical fiber 2.1, a doping 90.1, a polarization coupler 90.2 of an incoupling for a pilot beam 30 and of an outcoupling for a power monitoring 40, a power control 40.1, a remote control 60 or a system for evaluating backscattered and/or partially reflected working beams 70. Moreover, other participating users 200, such as other doctors, are able to follow an ophthalmological application online and participate in a supportive role in an ophthalmological intervention.

Upstream of end E of optical fiber 2.1, light-guide system 2 includes an application system 100.2, in which a slit lamp for ophthalmological applications is located. Moreover, application system 100.2 may include a link system for connecting an additional laser for use in selective laser trabeculotomy (SLT). A laser of this kind is operated in the PW mode and is preferably a laser array of active solid-state materials and/or of additional wavelength-influencing optical elements.

Working beams 20.1 and 20.2 emitted by semiconductor diode lasers 10.1 and 10.2 first propagate through a mechanico-optical system which has optical mirrors 80 and optically refractive elements. The two working beams 20.1 and 20.2 are deflected by optical mirrors 80 in such a way that they are coupled in at different locations on optical fiber 2.1 of light-guide system 2. However, they may equally be coupled in via only one optical mirror 80, or without any mirrors, at the same or different locations on optical fiber 2.1.

Subsequently thereto, first working beam 20.1 propagates through a doping 90.1 in optical fiber 2.1. This doping 90.1 has the effect of modifying the intensity and/or the wavelength of the working beams. Working beam 20.1 subsequently propagates through a polarization coupler 90.2 which polarizes working beam 20.1.

Propagating parallel thereto is working beam 20.2, which, in the example illustrated here, is deflected at mirror 80 and is coupled in at a downstream position on optical fiber 2.1. Working beam 20.2 subsequently propagates through polarization coupler 90.2. In this case as well, working beam 20.2, as well as working beam 20.1, undergo an appropriate selective polarization.

Working beam 20.1 also propagates through polarization coupler 90.2.

Subsequently thereto, in a simultaneous or temporally offset manner, both working beams pass that location where a pilot beam 30 is coupled in prior to an ophthalmological application.

At a later point in time, in a simultaneous or temporally offset manner, both working beams pass that location where a power control 40.1, a power monitoring 40, a remote control 60 or a system for evaluating backscattered and/or reflected working beams is connected.

Subsequently thereto, working beams 20.1 and 20.2 reach an application system 100.2. Located therein is a slit lamp, which is used to aid the ophthalmological application, since it permits simultaneous monitoring of the state of the eye during an ophthalmological application.

Subsequently thereto, at end E of optical fiber 2.1, working beams 20.1 and 20.2 propagate into application fiber 50 and, in the case of an ophthalmological application, then arrive directly at the eye to be treated.

It is also mentioned that power control 40.1, power monitoring 40, as well as the system for evaluating backscattered and/or reflected working beams are connected to control 100.1, and, if the values exceed or fall below those required for the ophthalmological treatment (energy too low/too high, power too high, reflection too great, . . . ), control 100.1 is driven to correct emitted working beams 20.1 or 20.2, and a suitable control software selectively controls semiconductor diode lasers 10.1 or 10.2.

Moreover, remote control 60 allows data to be transmitted in a wireless mode or with the aid of a network or the Internet to other users 200 participating in the ophthalmological application. It is thus possible, for example, for other doctors to participate in the ophthalmological treatment and to make appropriate recommendations and thus assist in an advisory capacity.

Moreover, user interface 100 allows a user of multiwavelength laser system 1 to manually control semiconductor diode lasers 10.1 and 10.2 at any time and, in this way, to adjust the relevant desired parameters for the ophthalmological application.

Moreover, via user interface 100, a user is able to switch off the multiwavelength laser system at any time and thus prevent any potential complications from occurring during an ophthalmological application.

By providing a device and a method for using a multiwavelength laser system for ophthalmological applications, the present invention has devised a multiwavelength laser system that is more compact and simpler to manipulate than multi-wavelength laser systems of the related art and that permits the simultaneous, temporally offset or spatially shifted application of a plurality of wavelengths, but also of different temporal regimes of the working beams for the ophthalmological laser therapy.

The present invention is not limited to the embodiments described herein; reference should be had to the appended claims.

The invention claimed is:

1. A multiwavelength semiconductor laser system for ophthalmological applications, the system comprising:
   a first semiconductor diode laser including a first working beam of a first wavelength;
   at least one second semiconductor diode laser having a second working beam of a second wavelength, the second wavelength different from the first wavelength, the first diode laser and the second diode laser each having a beam parameter product within a range between 0.1 and 125 mm*mrad;
   a light-guide system configured to couple the first working beam and second working beam such that each of the first and second working beams is directed to a retina of a patient; and
   a control configured to selectively activate one of the first semiconductor diode laser and second semiconductor diode laser such that a respective one of the first working beam and the second working beam is delivered from the light guide system to the retina of a patient for a therapy of the retina.

2. The multiwavelength laser system as recited in claim 1, wherein the first working beam and the second working beam each include a pulse duration.

3. The multiwavelength laser system as recited in claim 1, wherein at least one of the first diode laser and the second diode laser includes a crystal selected from the group consisting of: GaInAsSb, AlGaAsSb, AlAs, GaAs, GaP, InAs, AlGaInP, AlGaInP/GaAs, InP, doped garnets and doped vanadates.

4. The multiwavelength laser system as recited in claim 1, wherein each of the first wavelength and the second wavelength is within a spectral region selected from the group consisting of: 480 nm to 520 nm, 530 nm to 550 nm, 560 nm to 580 nm, 585 nm to 615 nm, 620 nm to 670 nm, 685 nm to 695 nm, 800 nm to 820 nm, and 1040 nm to 1070 nm.

5. The multiwavelength laser system as recited in claim 1, wherein the first working beam includes a first energy and the second working beam includes a second energy, the first energy different from the second energy.

6. The multiwavelength laser system as recited in claim 1, wherein each of the first working beam and the second working beam is emitted in one of a continuous wave mode and a pulsed wave mode.

7. The multiwavelength laser system as recited in claim 1, wherein the first working beam and the second working beam each have an energy that is between 10 µJ and 50 J.

8. The multiwavelength laser system as recited in claim 7, wherein the energy of the first working beam and the energy of the second working beam is between 0.5 mJ and 25 J.

9. The multiwavelength laser system as recited in claim 8, wherein the energy of the first working beam and the energy of the second working beam is less than 20 J.

10. The multiwavelength laser system as recited in claim 1, wherein the beam parameter product of each of the first diode laser and the second diode laser is between 1 and 100 mm*mrad.

11. The multiwavelength laser system as recited in claim 10, wherein the beam parameter product of each of the first diode laser and the second diode laser is between 2 and 80 mm*mrad.

12. The multiwavelength laser system as recited in claim 1, wherein at least one of the first working beam and the second working beam has a pulse duration between 1 femtosecond and 600 seconds.

13. The multiwavelength laser system as recited in claim 12, wherein the pulse duration is between 1 picosecond and 500 seconds.

14. The multiwavelength laser system as recited in claim 13, wherein the pulse duration is between 1 nanosecond and 300 seconds.

15. The multiwavelength laser system as recited in claim 1, wherein the first working beam and the second working beam are controlled separately.

16. A light-guide system for ophthalmological applications, comprising:
at least one fiber optic system;
a multiwavelength semiconductor laser system including a first semiconductor diode laser having a first working beam of a first wavelength, and at least one second semiconductor diode laser having a second working beam of a second wavelength, the second wavelength different from the first wavelength, the first diode laser and the second diode laser each having a beam parameter product within a range between 0.1 and 125 mm*mrad, the multiwavelength semiconductor laser system being coupled into the fiber optic system such that each of the first and second working beams is directed to a retina of a patient; and
a control configured to selectively activate one of the first semiconductor diode laser and second semiconductor diode laser such that a respective one of the first working beam and the second working beam is delivered from the fiber optic system to the retina of the patient for a therapy of the retina.

17. The light-guide system as recited in claim 16, wherein the at least one fiber optic system includes at least one optical fiber.

18. The light-guide system as recited in claim 16, wherein the at least one fiber optic system includes a fiber core having a numerical aperture between 0.01 and 0.4.

19. The light-guide system as recited in claim 18, wherein the numerical aperture is between 0.05 and 0.22.

20. The light-guide system as recited in claim 19, wherein the numerical aperture is between 0.07 and 0.15.

21. The light-guide system as recited in claim 16, further comprising a pilot beam coupleable into the fiber optic system.

22. The light-guide system as recited in claim 16, wherein the first working beam and the second working beam are at least partially coupled out of the fiber optic system.

23. The light-guide system as recited in claim 22, wherein the first working beam and the second working beam are at least partially coupled out into a power monitoring element.

24. The light-guide system as recited in claim 16, wherein at least one of the first diode laser and the second diode laser has at least one of an energy and power adjustable using a control element of a power control.

25. A method for performing an ophthalmological application, the method comprising:
providing a multiwavelength semiconductor laser system including a first semiconductor diode laser including a first working beam of a first wavelength and at least one second semiconductor diode laser having a second working beam of a second wavelength, the second wavelength different from the first wavelength, the first diode laser and the second diode laser each having a beam parameter product within a range between 0.1 and 125 mm*mrad; and
providing a light-guide system including at least one fiber-optic system, wherein the first working beam and the second working beam are coupleable into the light-guide system using the fiber-optic system;
activating the first semiconductor diode laser so as to perform a therapy of a retina of a patient; and
activating the second semiconductor diode laser independent of activating the first semiconductor diode laser so as to perform additional therapy of the retina.

\* \* \* \* \*